(12) United States Patent
Cimino

(10) Patent No.: US 6,379,326 B1
(45) Date of Patent: Apr. 30, 2002

(54) LIPOPLASTY METHOD

(76) Inventor: William Cimino, 578 W. Sagebrush Ct., Louisville, CO (US) 80027

( * ) Notice: Subject to any disclaimer, the term of this patent is extended or adjusted under 35 U.S.C. 154(b) by 0 days.

(21) Appl. No.: 09/412,489

(22) Filed: Oct. 5, 1999

Related U.S. Application Data

(63) Continuation-in-part of application No. 09/196,042, filed on Nov. 19, 1998, now Pat. No. 6,129,701.

(51) Int. Cl.⁷ ................................................ A61M 1/00
(52) U.S. Cl. ........................................... 604/35; 604/30
(58) Field of Search ........................ 604/27, 30, 32–35, 604/39, 404, 118, 119, 128, 129, 902, 500, 21; 607/97; 606/127, 128; 600/459

(56) References Cited

U.S. PATENT DOCUMENTS

| | | | |
|---|---|---|---|
| 4,548,197 A | * 10/1985 | Kinoshita | ...................... 128/4 |
| 4,596,533 A | * 6/1986 | Lee | |
| 4,735,605 A | * 4/1988 | Schwartz | |
| 4,886,491 A | * 12/1989 | Parisi et al. | .................. 604/22 |
| 5,013,300 A | * 5/1991 | Williams | |
| 5,112,302 A | * 5/1992 | Cucin | |
| 5,163,433 A | * 11/1992 | Kagawa et al. | ........ 128/660.01 |
| 5,181,907 A | * 1/1993 | Becker | |
| 5,348,535 A | * 9/1994 | Cucin | |
| 5,429,596 A | * 7/1995 | Arias et al. | .................... 604/21 |
| 5,447,494 A | * 9/1995 | Doresy, III | .................. 604/43 |
| 5,527,273 A | * 6/1996 | Manna et al. | ................. 604/22 |
| 5,569,178 A | * 10/1996 | Henley | |
| 5,643,198 A | * 7/1997 | Cucin | .......................... 604/22 |
| 5,665,101 A | * 9/1997 | Becker | |
| 5,766,194 A | * 6/1998 | Smith | .......................... 606/167 |
| 6,129,701 A | * 10/2000 | Cimino | ........................ 604/35 |

* cited by examiner

Primary Examiner—Sharon Kennedy
(74) Attorney, Agent, or Firm—Merchant & Gould P.C.; Thomas H. Young

(57) ABSTRACT

An improved method of fragmenting and removing soft tissues of a patient is disclosed. More particularly, the method includes steps for the surgical removal of unwanted fatty tissues using an ultrasonic frequency vibratory probe and a separate multi-lumen suction and irrigation cannula. The ultrasonic frequency vibratory probe and the multi-lumen suction and irrigation cannula are separate instruments that are used to separate the tissue fragmentation and removal processes, thereby decreasing procedure time and reducing trauma to tissues.

28 Claims, 3 Drawing Sheets

LIPOPLASTY METHOD

CROSS-REFERENCE TO RELATED APPLICATION

The present application is a continuation-in-part of U.S. Ser. No. 09/196,042 filed Nov. 19, 1998, entitled "Vented Aspirator and Method," now U.S. Pat. No. 6,129,701, issued Oct. 19, 2000.

BACKGROUND OF THE INVENTION

This invention relates generally to a method of fragmenting and removing soft tissue, and, more particularly, to a method for the removal of unwanted fatty tissues that involves the use of an ultrasonic frequency vibrating probe and a multi-lumen suction and irrigation cannula.

Liposuction is a surgical procedure for altering the human form, specifically by removal of localized deposits of fat tissues that are unresponsive to diet or exercise. The procedure is also known as suction lipectomy, lipoplasty, lipolysis, suction-assisted lipoplasty, and more recently as body contour surgery or body sculpting surgery. It is most often performed by plastic surgeons, although dermatologists, gynecologists, and other surgical specialties also perform the procedure.

The procedure is typically accomplished by inserting a small cannula or metal tube through an incision in the skin, applying a suction source to the end of the cannula that remains outside of the body, and forcing the working end of the cannula forward and backward in the layer of fatty tissue. The fatty tissue is torn, crushed, or avulsed, and is then aspirated through small openings along the sides of the cannula near the tip and then through a central lumen in the cannula to a tissue canister placed in-line with the cannula and the suction source. The procedure can involve multiple incisions and many passes of the cannula in each incision to achieve the desired cosmetic effect for the patient.

The liposuction procedure can be traumatic to the patient. The mechanical disruption of the tissues can result in, among other things, bleeding, bruising, temporary numbness, or swelling. The procedure can also be physically demanding on the surgeon because of the forces required to repeatedly push the cannula through the tissue. Further, the final cosmetic result is a function of the skill of the surgeon, the patient, and the type of surgical instrumentation used in the surgery.

Recently, efforts have been made to combine ultrasonic vibrations with the liposuction cannula to improve upon the tissue discrimination capability of the liposuction cannula and to provide an instrument that removes adipose tissue faster and more uniformly than current liposuction cannulae. This procedure is commonly referred to as ultrasound-assisted lipoplasty. In a typical ultrasound-assisted lipoplasty procedure, an ultrasonically vibrating cannula is inserted through an incision in the patient's skin and passed forward and backward through the adipose tissue layer. The ultrasonically vibrating cannula fragments the adipose tissues, which are then typically aspirated through a central lumen in the ultrasonically vibrating cannula.

Numerous patents disclose methods and apparatus for ultrasound-assisted removal of adipose tissue from the human body. U.S. Pat. No. 4,886,491 (Dec. 12, 1989) to Parisi has a method of removing fatty tissue from a patient using an ultrasonic probe to melt at least some of the fatty tissue. The method and apparatus disclosed in this patent uses an ultrasonic frequency vibrating probe that includes an aspiration channel in the probe for the purpose of aspirating fragmented tissues.

U.S. Pat. No. 5,419,761 to Narayanan (May 30, 1995) discloses an ultrasonic handpiece with a rigid tube with an axially extending lumen.

U.S. Pat. No. 5,244,458 to Takasu (Sep. 14, 1993) has an ultrasonic handpiece with a hollow cannula with a plurality of suction openings in the cannula. U.S. Pat. No. 5,236,414 (Aug. 17, 1993) also to Takasu has an ultrasonic handpiece with a tip having a tubular body and a suction passage. U.S. Pat. No. 5,514,086 (May, 1996) to Parisi has an ultrasonic handpiece with a probe and a tip on the probe with an acoustic impedance substantially greater than that of the probe. U.S. Pat. No. 5,527,273 (Jun. 18, 1996) to Manna has an ultrasonic lipectomy probe with an enlarged head on the distal end and a longitudinally extending channel in the probe.

The use of a solid ultrasonic probe followed by the use of a single lumen suction cannula is known, as disclosed in "Ultrasonic Assisted Lipoplasty, Technical Refinements and Clinical Evaluations", Michele L. Zocchi, *Clinics in Plastic Surgery*, Volume 23, Number 4, pages 575–598, October, 1996.

Combining the ultrasonic vibration probe and the suction cannula in a single instrument has the following disadvantages. First, in order to minimize the required incision size the outside diameter of the ultrasonic/suction probe must be kept to a minimum, typically 4–5 mm. This limits the diameter of the inner suction lumen, which is typically about 2 mm. These probes are typically from 20–30 cm in length. This creates a long, small diameter suction lumen that provides poor performance for removing viscous emulsified fatty tissues. Second, fabricating these ultrasonic probes with suction lumens requires a process known as 'gun-drilling', a process which makes the probes expensive and difficult to manufacture. Third, and most importantly, the liposuction procedure is a "closed-procedure", meaning that the instruments are passed through small incisions in the skin and the functioning tip of the instrument is not under direct visualization. The skin and fatty tissues that surround the length of the ultrasonic probe create a pressure seal that prevents the flow of ambient pressure fluids such as air to the operative site. Thus the suction process is very inefficient and ineffective because the pressure at the operative site is quickly reduced to that of the suction source, eliminating any pressure differential, and causing the flow of fragmented tissue and fluid to stop, a phenomenon which appears to the operator as a "clogged" instrument.

A comparison of the suction-assisted liposuction and ultrasound-assisted lipoplasty approaches with currently available surgical instruments for both procedures was recently given in *Ultrasound—Assisted Lipoplasty Resource Guide*, published in PlasticSurgery News, a publication of The American Society of Plastic and Reconstructive Surgeons, 1997. In the article the author cites the disadvantages of the current ultrasound-assisted lipoplasty procedure compared to the suction-assisted liposuction procedure as: 1) burns of the skin are possible, 2) longer incisions are needed, 3) seromas are more common, 4) longer operating times, and 5) greater expense.

Thus there is a need for a method of removing unwanted soft tissue, particularly fatty tissues, which permits the surgeon to work more quickly by minimizing clogging of the instruments and also reduces the potential for burns or seroma formation.

SUMMARY OF THE INVENTION

In one aspect, the present invention comprises a method for removing unwanted fatty tissues from a patient by creating a small incision in the skin of the patient, inserting an infusion probe through the incision into the patient's fatty tissues, and infusing a wetting solution into the fatty tissues. The infusion probe is removed and an ultrasonic frequency vibratory probe is inserted through the incision and into the fatty tissues of the patient. The ultrasonic probe is activated to impart ultrasonic frequency vibratory energy to the fatty tissues causing the fatty tissues to fragment. The ultrasonic frequency vibratory probe is removed and a multi-lumen suction and irrigation cannula is inserted through the incision and into the same region of fatty tissues of the patient. Suction and irrigation are provided through the multi-lumen suction and irrigation cannula to effect removal of the fragmented tissues. The multi-lumen suction and irrigation cannula is removed from the patient and the incision in the skin is closed.

In another aspect, the foregoing method further comprises simultaneously providing suction and irrigation to the multi-lumen cannula.

In another aspect, the method involves sequentially providing suction and irrigation to the multi-lumen suction and irrigation cannula.

In a further aspect, the method further comprises providing ultrasonic frequency vibratory energy in a series of profiled pulses.

In another aspect, the method further comprises emulsifying at least a portion of the fragmented fatty tissue.

BRIEF DESCRIPTION OF THE DRAWINGS

The invention can be understood by reference to the following figures when read in conjunction with the detailed description of the invention.

DETAILED DESCRIPTION OF THE INVENTION

Figure 1:
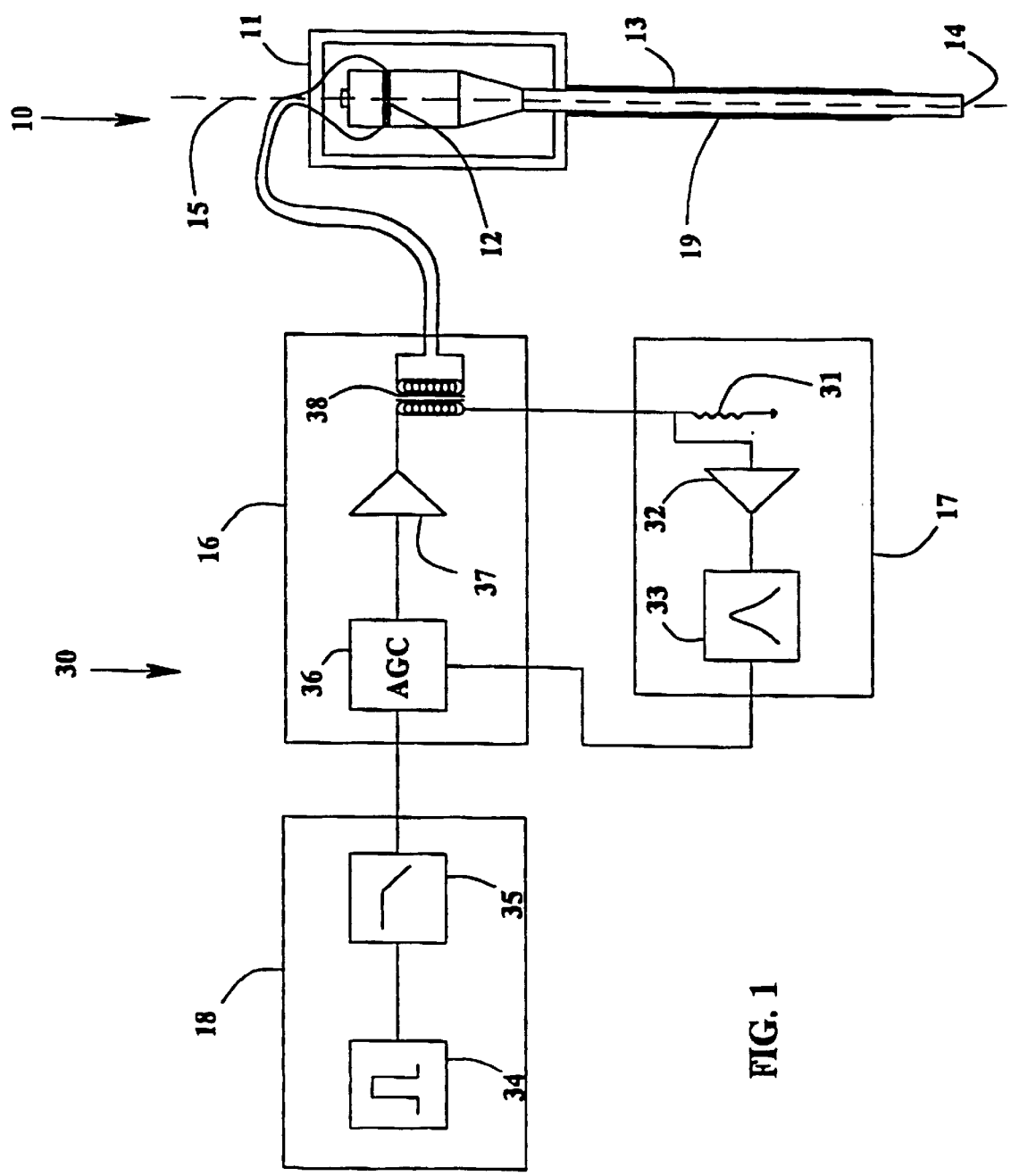
FIG. 1 is a functional block diagram and partial circuit diagram of an ultrasonic surgical apparatus for the delivery of ultrasonic frequency vibratory energy.

As described below, the instant method provides a solution to the problems encountered by prior ultrasound-assisted lipoplasty procedures including poor removal of viscous fatty tissues due to the small lumen diameter in multipurpose ultrasonically vibrating cannula and the high cost of manufacture of multipurpose ultrasonically vibrating cannula. A multipurpose ultrasonically vibrating cannula is a cannula that is capable of aspirating fragmented tissue and fluids through an aspiration channel and is also capable of ultrasonic frequency vibration along its length. Most importantly by providing an irrigation function in conjunction with tissue aspiration, the present method eliminates the pressure seal that causes the plugging and "clogged" instruments encountered in the prior liposuction methods.

The term "wetting solution" is used herein to refer to the fluid that is introduced into the patient prior to introduction of the ultrasonic applicator (described in more detail herein below). The term "irrigation solution" is used herein to refer to the fluid that is introduced subsequent to introduction of the ultrasonic applicator. It can be the same fluid as the wetting solution. The fluid useful as a wetting solution or an irrigation solution is a solution that is composed primarily of a biocompatible fluid such as saline solution or Ringer's Lactate. Combined with the fluid optionally can be medications for purposes such as pain suppression or vasoconstriction. Typically in liposuction procedures, a local anesthetic such as lidocaine is introduced for pain suppression. Also it is typical to introduce a vasoconstriction agent such as epinephrine to help control local bleeding and resulting bruising. Under normal operation the same fluid composition is used as a wetting solution and as an irrigation solution; however, if desired, the composition of the irrigation solution can differ by the addition of other medications or different concentrations of medications from that used in the wetting solution. Of course all such fluids are administered under sterile conditions.

The term "infusion probe" is used herein to mean a cannula, or tube having at least one lumen, designed for the delivery of fluids to the tissues of a patient. Typically the wetting solution is introduced through the infusion probe into the targeted tissues of the patient.

In operation of the instant method, a skilled medical person, normally a surgeon, creates a small incision in the skin of a patient in the target area. Since the present method is particularly useful for removal of unwanted adipose tissue from a patient, the description of the present method will be made with reference to removal of such fatty tissue.

After creation of the incision, an infusion probe is inserted through the incision and into the targeted fatty tissue. Wetting solution is infused into the targeted fatty tissue to create a region containing wetting solution, hereinafter referred to as the "target zone". Normally this is accomplished by pumping the wetting solution through the infusion probe and into the target zone under pressure with flow rates from about 50 milliliters per minute to 500 milliliters per minute using, for example, a peristaltic pump system. The quantity of wetting solution administered is controlled by the medical personnel. Normally this is determined by correlating the amount of wetting solution to be administered with the estimated amount of fatty tissue to be removed, usually using an approximate 1:1 ratio.

Upon administration of the desired amount of wetting solution, the infusion probe is removed. An ultrasonic frequency vibratory probe (also referred to interchangeably herein as an ultrasonic applicator or ultrasonic probe) is inserted into the target zone of the patient in which the wetting solution has been infused. The ultrasonic frequency vibratory probe can be a multi-purpose ultrasonically vibrating cannula or it can preferably be a solid ultrasonically vibrating probe. When the ultrasonic probe is appropriately positioned, it is activated as described in more detail below to impart ultrasonic frequency vibratory energy to the fatty tissues in the target zone. Application of such energy causes the fatty tissue to be fragmented or disrupted. It is preferred that sufficient vibratory energy be administered to form an emulsion with the disrupted fatty tissue and the wetting solution. Formation of such an emulsion expedites removal of the fatty tissue from the patient during the aspiration step which follows. In a typical operation, some of the fatty tissue is not fully emulsified and remains as particulates or pieces of tissue. The present method in which an irrigation solution is administered helps expedite removal of such non-emulsified pieces of tissue.

In a normal procedure, the operator of the ultrasonic probe moves the probe in the target zone to fragment the fatty tissue in that region. Typically this is accomplished using a longitudinally reciprocal movement of the prove. Once sufficient fragmentation has been accomplished as determined by the surgeon, the ultrasonic probe is removed and a multi-lumen suction and irrigation cannula is inserted into the target zone. This cannula is used to provide both aspiration of tissue and fluid from the target zone and introduction of irrigation solution into the target zone. Once the multi-lumen Suction and irrigation cannula is in place, the tissue aspiration and irrigation functions can be activated in any desired order including sequentially or simultaneously.

Tissue removal is accomplished by providing suction to a lumen in the cannula. Irrigation solution is introduced through a different lumen in the same cannula. The tissue removal process and introduction of irrigation solution can be accomplished simultaneously or sequentially as desired by the operator. When sequential operation is effected, irrigation fluid is pumped into the target zone to slightly pressurize the local subcutaneous space and to provide additional free fluid for the formation of emulsion. Suction can then be applied to remove the emulsion and tissue fragments. This process can also be effected simultaneously so that there is a continuous addition and removal of irrigation fluid that mixes with the fragmented tissues and emulsion. The suction and irrigation processes normally continue until the aspirate no longer contains clinically significant amounts of fragmented tissues or emulsion as determined by the surgeon who views the aspirate color and viscosity in the suction tubing.

Once the appropriate level of tissue removal has been achieved, the multi-lumen suction and irrigation cannula is removed from the patient. The incision in the skin of the patient is typically closed and the procedure is complete. If necessary, the incision can be left open and fluid drains inserted to aid in removal of fluids that might accumulate post procedure.

In operation of the ultrasonic frequency vibratory probe, longitudinal vibration is established in the ultrasonic surgical handpiece and ultrasonic probe. An ultrasonic motor converts ultrasonic frequency electrical energy to ultrasonic frequency vibrational energy in the ultrasonic surgical handpiece. The ultrasonic frequency vibrational energy is coupled to the ultrasonic probe. Elastic stresses in the probe material generally determine the upper limit of vibration amplitude. For example, with a preferred titanium alloy material, Ti6A14V, it is preferred to keep the maximum peak vibratory stresses below about 40 ksi (kilopound per square inch) in order to prevent fatigue cracking in the probe. The ultrasonic motor and ultrasonic probe in combination have a preferred resonant frequency. The preferred resonant frequency is largely determined by the overall longitudinal length of the assembled ultrasonic motor and ultrasonic probe. For a simple constant cross-sectional beam or rod, the relationship between frequency and length can be approximated using the equation: $c = f * \lambda$ where c is the speed of sound in the material, f is the frequency in Hz, and $\lambda$ is the wavelength. Tapered sections and other shaped transition sections affect the resonant frequency and are generally analyzed using a finite element method, as is well known to those skilled in the art. The frequency is maintained at a specific frequency between 20 kilohertz (kHz) and about 80 kHz, preferably 20 kHz to 40 kHz. The specific frequency can drift with temperature or loading conditions. This can be monitored and controlled using the monitor circuit described herein below.

The ultrasonic applicator can be operated in a continuous mode in which vibratory energy is supplied continuously while the applicator is engaged with the target tissue. Alternatively, and in the preferred mode of operation, the vibratory energy can be pulsed.

The pulsing of vibratory energy is described in copending U.S. patent application Ser. No. 09/260,297 which is incorporated herein by reference in its entirety.

In the pulsed method of operation, a first time portion of a pulse of ultrasonic frequency vibratory energy is profiled and kept below an upper limit of about fifty milliseconds. A second time portion of the pulse of ultrasonic frequency vibratory energy that follows the first time portion is at least three times the time duration of the first time portion while the maximum vibratory amplitude is at least twice but not more than twenty times the minimum vibratory amplitude. The first profile is the shape of the leading edge of the profiled pulse signal as it ascends from the minimum magnitude to the maximum magnitude. The second profile is the shape of the trailing edge of the profiled pulse signal as it descends from the maximum magnitude to the minimum magnitude. The first time portion is normally between one millisecond and fifty milliseconds in duration.

Apparatus useful in providing the ultrasonic frequency vibratory energy and applying it to target tissue is described in more detail below. In connection with Such apparatus, a power control circuit is electrically connected to an ultrasonic motor for supplying electrical power to the ultrasonic motor to produce ultrasonic frequency vibratory energy at a resonant frequency that is applied to the ultrasonic applicator to produce vibratory motion in the applicator.

A vibration monitor circuit is electrically connected to the power control circuit for measuring an electrical vibration signal at the resonant frequency and proportional to a vibratory amplitude of the ultrasonic applicator so that the power control circuit supplies electrical power to the ultrasonic motor at the resonant frequency. The electrical vibration signal can be proportional to a current or a voltage of the electrical power supplied to the ultrasonic motor by the power control circuit or it can be generated by a vibration sensing transducer located in or near the ultrasonic motor.

A profile generator circuit is electrically connected to the power control for producing a profiled pulse signal with a first profile and a maximum magnitude during a first time portion and a second profile and a minimum magnitude during a second time portion. The first time portion is generally the rising portion plus the time at maximum magnitude of the profiled pulse signal and the second time portion is generally the falling portion plus the time at minimum magnitude of the profiled pulse signal.

Referring now to the drawings, FIG. 1 is a functional block diagram and partial circuit diagram of an ultrasonic surgical apparatus 10 and circuits 30 for delivery of ultrasonic frequency vibratory energy to the tissues of a patient. The ultrasonic surgical apparatus 10 includes a housing 11 to be held and manipulated by a user, an ultrasonic motor 12 supported within the housing 11, and an ultrasonic applicator 13 operatively connected to the ultrasonic motor 12 and extending beyond the housing 11. In FIG. 1 the ultrasonic applicator 13 depicted is an elongate probe. Particularly preferred ultrasonic probes are disclosed in copending and commonly assigned U.S. patent application Ser. No. 09/169, 393, incorporated herein by reference in its entirety. Preferably the ultrasonic probe has a longitudinal shank that is round in cross-section. The preferred shape of the tip of the probe is blunt or bullet-nosed with smooth and rounded edges about and around the circumference where the tip is attached to the shank of the probe. Most preferably these are one or more grooves substantially circumscribing that portion of the shank immediately adjacent to the tip, the grooves being generally transverse to the longitudinal axis of the shank.

The housing 11 can be fabricated from metals or plastics, the preferred materials are steam sterilizable plastics such as Delrin® (an acetal homopolymer) or Radel® (a polyphenylsulphone). (Delrin is a registered trademark of DuPont and Radel is a registered trademark of Amoco) The ultrasonic motor 12 can be constructed from piezoelectric ceramics or magnetostrictive metals. The preferred materials are piezoelectric ceramics such as PZT-4 or PZT-8. These are described in "Guide to Modern Piezoelectric Ceramics", Morgan Matroc, Inc., Electro Ceramics Division, 232 Forbes Road, Bedford, Ohio 44146. The ultrasonic applicator 13 can be fabricated from metal materials such as 6065 or 7075 aluminum, stainless steel, or titanium. The preferred materials for the ultrasonic applicator 13 are titanium or titanium alloys such as Ti6A14V. In combination, the ultrasonic motor 12 and the ultrasonic applicator 13 have a resonant frequency. The resonant frequency is the frequency of preferred longitudinal vibration.

The ultrasonic applicator 13 has a distal surface 14 for engagement with tissues of a patient. The distal surface 14 can be shaped to achieve a desired surgical effect with preferred shapes described hereinabove. The ultrasonic motor 12 and the ultrasonic applicator 13 can be disposed along and are symmetric about an axis 15. A protective sleeve 19 can be located about and along the ultrasonic applicator 13 to protect the tissues of the patient from unnecessary injury due to contact about and along the length of the ultrasonic applicator 13. The sleeve terminates on the distal end of the ultrasonic applicator at or near the most distal vibratory node of the elongate ultrasonic probe. Preferably, the termination on the sleeve has an inside diameter that is no smaller and substantially the same as the outside diameter of the ultrasonic applicator 13 to form a barrier to the passage of material into space between the sleeve and applicator 13. Alternatively, space between the ultrasonic applicator and the termination on the end of the sleeve adjacent to the tip of the applicator can be sealed with a sealing means such as glue, a flange, or an o-ring. Particularly preferred protective sleeves are disclosed in commonly assigned U.S. patent application Ser. No. 09/191, 807, incorporated herein by reference in its entirety.

The ultrasonic motor 12 can be assembled as described in the art such as U.S. Pat. No. 3,990,452 of Murry (Nov. 9, 1976); U.S. Pat. No. 5,391,144 of Sakurai (February, 1995); U.S. Pat. No. 5,312,329 of Beaty (May, 1994); U.S. Pat. No. 5,449,370 of Vaitekunas (September, 1995); U.S. Pat. No. 5,465,468 of Manna (November, 1995). Preferably the ultrasonic motor is constructed using an even number of washers of PZT-4 or PZT-8 assembled in a stack, with the polarity of every other washer reversed. The preferred dimensions of the PZT washers are between 0.5 inches and 1.0 inches in diameter and between 0.05 inches and 0.10 inches thick. A flat, thin, washer-shaped electrode, typically fabricated of beryllium copper with a thickness between 0.001 and 0.003 inches, is placed between each PZT washer. Every other electrode is electrically tied together, resulting in two electrical leads to the ultrasonic motor 12. The stack of PZT washers is placed under compression using a compression bolt that passes through the center of the PZT washers. It is preferred to locate the center of the stack of PZT washers at a location of maximum elastic stress due to the longitudinal vibration in the assembled ultrasonic surgical handpiece.

A power control circuit 16 is electrically connected to the ultrasonic motor 12 for supplying electrical power to the ultrasonic motor 12 to produce ultrasonic frequency vibratory energy that is applied to the ultrasonic applicator 13 to produce vibratory motion in said ultrasonic applicator. An automatic gain control element 36 receives an electrical vibration signal from a vibration monitor circuit 17 and a vibration amplitude command signal from a profile generator circuit 18. The vibration amplitude command can be a pulsed signal or it can be a constant level signal. The automatic gain control element 36 adjusts the input to a power amplifier 37 so that electrical power is supplied to the ultrasonic motor 12 through an output transformer 38 at the resonant frequency to produce ultrasonic frequency vibratory energy. A preferred embodiment of the circuit elements of the automatic gain control element 36 is shown in the application notes for the Analog Devices 633, an integrated circuit multiplier, 1992 Analog Devices Special Linear Reference Manual, page 2–52, 53. In an alternative embodiment, the automatic gain control element 36 can be replaced with an automatic phase control element that includes a phase-locked-loop circuit that maintains a selected phase relationship between the electrical vibration signal and a reference signal.

The vibration monitor circuit 17 is electrically connected to the power control circuit 16 for measuring an electrical vibration signal at the resonant frequency and proportional to a vibratory amplitude of the ultrasonic applicator 13. The preferred electrical vibration signal is proportional to a current of the electrical power supplied by the power control circuit 16. A current sense resistor 31 can be located in-line with the primary of the output transformer 38. The voltage across the current sense resistor 31 is applied to and amplified by a signal amplifier 32 and the output of the signal amplifier 32 is applied to a band-pass filter 33. The output of the band-pass filter 33 is the electrical vibration signal that is in electrical communication with the power control circuit 16.

The profile generator circuit 18 is electrically connected to the power control circuit 16 for producing a profiled pulse signal. A digital pulse generator 34 generates a pulse signal that is applied to a low-pass filter 35. The low-pass filter 35 profiles the leading and trailing edges of the pulse signal generated by the digital pulse generator 34. The output of the low-pass filter 35 is the profiled pulse signal that is in electrical communication with the power control circuit 16.

Figure 2:
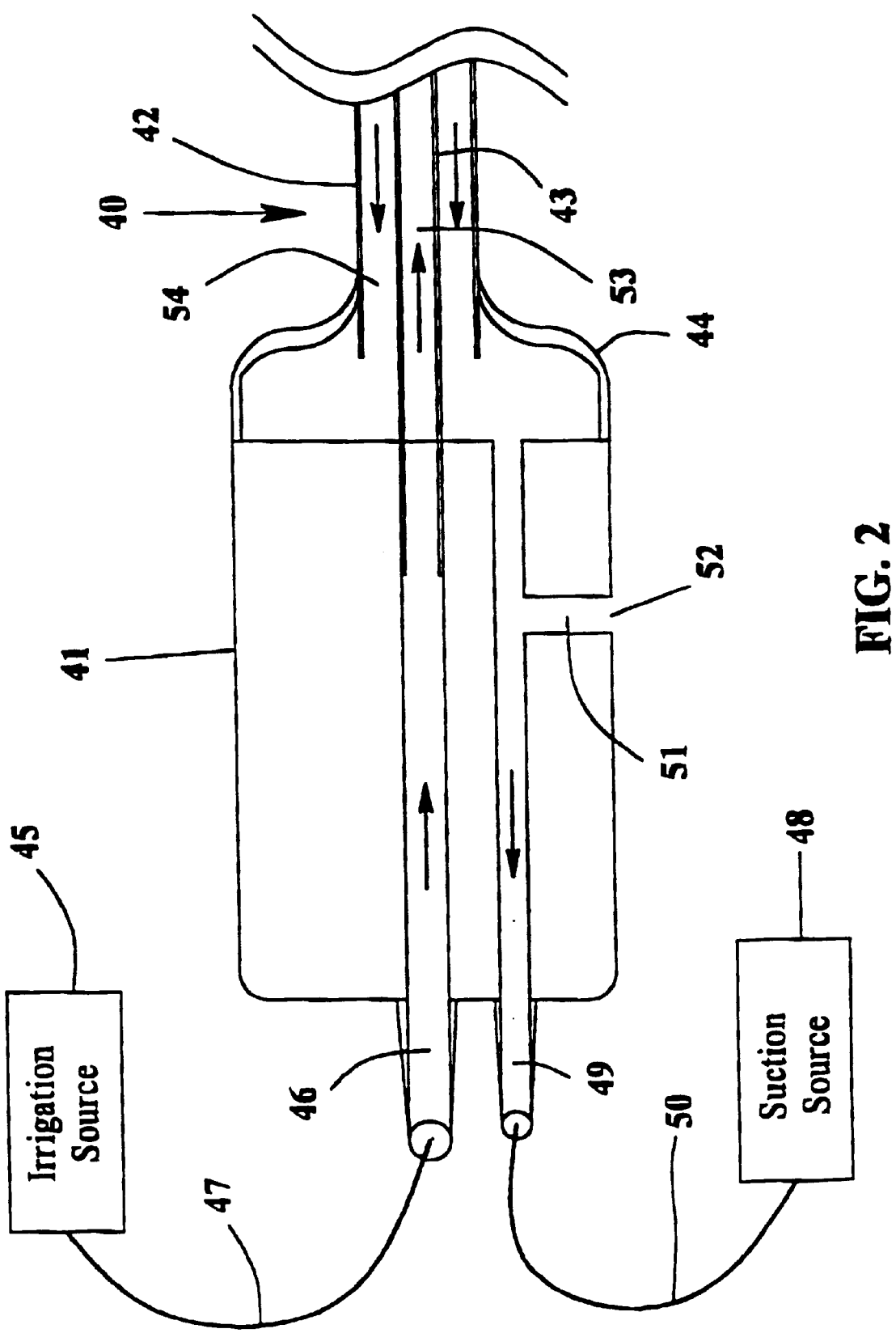
FIG. 2 is a partial schematic representation of the proximal end of the multi-lumen suction and irrigation cannula attached to the suction/irrigation handpiece.

Referring to FIG. 2, the proximal end of multi-lumen suction and irrigation cannula 40 is attached to suction and irrigation handle 41. Multi-lumen suction and irrigation cannula 40 has an outer tube 42 and an inner tube 43. A locking collar 44 attaches multi-lumen suction and irrigation cannula 40 to suction and irrigation handle 41. An irrigation source 45 is in fluid communication with irrigation channel 46 in suction and irrigation handle 41 through irrigation tubing 47. A suction source 48 is in fluid communication with suction channel 49 in suction and irrigation handle 41 through suction tubing 50. Irrigation channel 46 is in fluid communication with irrigation lumen 53 of inner tube 43. Suction channel 49 is in fluid communication with suction lumen 54 formed between inner tube 43 and outer tube 42. Vent passage 51 is in fluid communication with suction channel 49 and the ambient air about suction and irrigation handle 41.

Preferably the outside diameter for the multi-lumen cannula is between about three and about six millimeters. The suction lumen has a resistive ratio that is determined by dividing the surface area of a unit length of the lumen by the cross-sectional area of the lumen. Similarly the resistive ratio of the irrigation lumen is determined by dividing a unit length of this lumen by its cross-sectional area. Preferably the resistive ratio of the suction lumen is between about 0.5 and 1.5 times the resistive ratio of the irrigation lumen. Most preferably the value is slightly less than 1.0 to account for the increase in viscosity of the aspirate relative to the irrigation solution. Such a value provides that approximately the same amount of fluid is removed as is being injected. While it is contemplated that three or more lumen can be used, it is preferred that the suction and irrigation cannula has two lumen with one lumen used for suction and the other used to provide irrigation solution.

The vent passage can be opened or closed by covering vent passage opening 52 with a thumb or finger or alternatively by using a valve that can be manually or remotely activated. Opening the vent passage allows ambient air to enter the suction tubing which can rapidly clear the tube. If there is concern about the possible introduction of pathogens into the target zone, a sterilized source of ambient air or inert gas can be provided.

Figure 3:
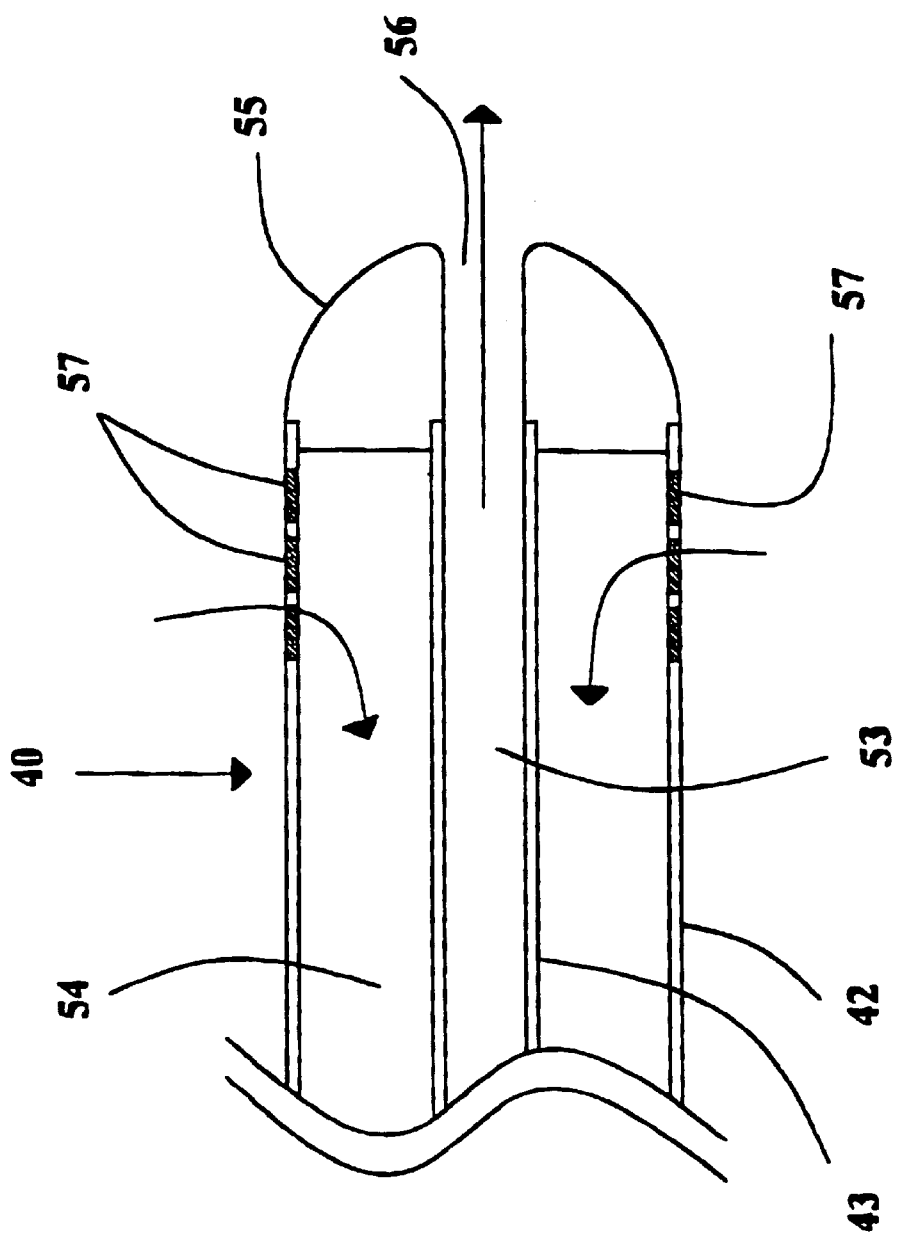
FIG. 3 is a partial schematic representation of the distal end of the multi-lumen suction and irrigation cannula.

FIG. 3 depicts a preferred embodiment for the distal end of multi-lumen suction and irrigation cannula 40. A multi-lumen suction and irrigation cannula is shown with an outer tube 42 and an inner tube 43. The cannula has a tip 55 that is attached to inner tube 3 and outer tube 42. An irrigation port 56 in tip 55 is in fluid communication with irrigation lumen 53. Suction ports 57 in the wall of outer tube 42 create fluid communication between the area along and about the distal end of the multi-lumen suction and irrigation cannula and suction channel 54.

While the invention has been described in connection with what is presently considered to be the most practical and preferred embodiments, it is to be understood that the invention is not to be limited to the disclosed embodiments, but is intended to cover various modifications and equivalents included within the spirit and scope of the appended claims.

What is claimed is:

1. A method for removing fatty tissues from a patient which comprises:

creating an incision in the skin of a patient;

inserting an ultrasonic frequency vibratory probe through the incision and into the target zone;

activating said ultrasonic frequency vibratory probe to provide ultrasonic frequency vibratory energy to fatty tissue in said target zone to form fragmented fatty tissue in said target zone;

removing the ultrasonic frequency vibratory probe;

inserting a multi-lumen suction and irrigation cannula having a distal end and a proximal end through the incision, the distal end placed into the target zone and the proximal end remaining outside the incision;

applying suction to the proximal end of a first lumen in said multi-lumen suction and irrigation cannula to remove fragmented fatty tissue;

providing irrigation solution into the proximal end of a second lumen in said multi-lumen suction and irrigation cannula and out of the distal end of said second lumen into said target zone; and removing said cannula from said patient.

2. The method of claim 1 wherein the application of suction is alternated with the introduction of irrigation solution.

3. The method of claim 2 wherein suction is applied simultaneously with the introduction of irrigation solution.

4. The method of claim 1 wherein sufficient ultrasonic frequency vibratory energy is provided to form an emulsion with at least a portion of said fragmented fatty tissue and infused wetting solution.

5. The method of claim 1 wherein the incision in the skin of the patient is closed following removal of the cannula.

6. The method of claim 1 wherein said ultrasonic frequency vibratory energy is provided as a plurality of pulses.

7. The method of claim 6 wherein said pulses are in the form of profiled pulse signals.

8. The method of claim 7 wherein said profiled pulse signals comprise a first profile having a maximum magnitude during a first time portion and a second profile having a minimum magnitude during a second time portion, said second time portion being greater than three times the duration for the first time portion and said maximum magnitude being between two and twenty times said minimum magnitude.

9. The method of claim 8 wherein said first time portion is between on millisecond and fifty milliseconds in duration.

10. The method of claim 1 wherein said irrigation solution comprises sterile saline solution or sterile Ringer's Lactate.

11. The method of claim 10 wherein said irrigation solution further comprises an anesthetic.

12. The method of claim 10 wherein said irrigation solution further comprises a vascoconstricter.

13. The method of claim 10 wherein said irrigation solution comprises a local anesthetic and a vascoconstricter.

14. A method for removing fatty tissues from a patient which comprises:

creating an incision in the skin of a patient;

inserting an infusion probe through the incision and into fatty tissues of the patient;

infusing a wetting solution into the fatty tissues to create a target zone in the fatty tissues;

removing the infusion probe;

inserting an ultrasonic frequency vibratory probe through the incision and into the target zone;

activating said ultrasonic frequency vibratory probe to provide ultrasonic frequency vibratory energy to fatty tissue in said target zone to form fragmented fatty tissue in said target zone;

removing the ultrasonic frequency vibratory probe;

inserting a multi-lumen suction and irrigation cannula having a distal end and a proximal end through the incision, the distal end placed into the target zone and the proximal end remaining outside the incision;

applying suction to the proximal end of a first lumen in said multi-lumen suction and irrigation cannula to remove fragmented fatty tissue;

providing irrigation solution into the proximal end of a second lumen in said multi-lumen suction and irrigation cannula and out of the distal end of said second lumen into said target zone; and removing said cannula from said patient.

15. The method of claim 14 wherein the application of suction is alternated with the introduction of irrigation solution.

16. The method of claim 15 wherein suction is applied simultaneously with the introduction of irrigation solution.

17. The method of claim 14 wherein sufficient ultrasonic frequency vibratory energy is provided to form an emulsion with at least a portion of said fragmented fatty tissue and infused wetting solution.

18. The method of claim 14 wherein the incision in the skin of the patient is closed following removal of the cannula.

19. The method of claim 14 wherein said ultrasonic frequency vibratory energy is provided as a plurality of pulses.

20. The method of claim 19 wherein said pulses are in the form of profiled pulse signals.

21. The method of claim 20 wherein said profiled pulse signals comprise a first profile having a maximum magnitude during a first time portion and a second profile having a minimum magnitude during a second time portion, said second time portion being greater than three times the duration for the first time portion and said maximum magnitude being between two and twenty times said minimum magnitude.

22. The method of claim 21 wherein said first time portion is between on millisecond and fifty milliseconds in duration.

23. The method of claim 14 wherein said irrigation solution comprises sterile saline solution or sterile Ringer's Lactate.

24. The method of claim 23 wherein said irrigation solution further comprises an anesthetic.

25. The method of claim 23 wherein said irrigation solution further comprises a vascoconstricter.

26. The method of claim 23 wherein said irrigation solution comprises a local anesthetic and a vascoconstricter.

27. The method of claim 14 wherein the infusion probe is a multi-lumen cannula.

28. The method of claim 27 wherein the wetting solution is infused into the fatty tissue through at least one lumen in said multi-lumen suction and irrigation cannula.

* * * * *